United States Patent [19]

Iimuro et al.

[11] Patent Number: 4,950,804

[45] Date of Patent: Aug. 21, 1990

[54] PROCESS FOR PREPARING BISPHENOL A

[75] Inventors: Shigeru Iimuro; Yoshio Morimoto; Takashi Kitamura, all of Aichi, Japan

[73] Assignee: Mitsui Toatsu Chemicals, Inc., Tokyo, Japan

[21] Appl. No.: 310,350

[22] Filed: Feb. 14, 1989

[30] Foreign Application Priority Data

Feb. 19, 1988 [JP] Japan ................... 63-35120

[51] Int. Cl.$^5$ ..................... C07C 37/20; C07C 37/70; C07C 39/16
[52] U.S. Cl. .................................... 568/727
[58] Field of Search .............. 568/724, 722, 727, 728, 568/723, 749, 751

[56] References Cited

U.S. PATENT DOCUMENTS

| | | | |
|---|---|---|---|
| 3,073,868 | 1/1963 | Prahl et al. | 568/727 |
| 3,221,061 | 11/1965 | Grover et al. | 568/728 |
| 4,191,843 | 3/1980 | Kwantes | 568/728 |
| 4,364,099 | 12/1982 | Faler | 568/726 |
| 4,443,653 | 4/1984 | McLaughlin | 568/727 |

FOREIGN PATENT DOCUMENTS

| | | | |
|---|---|---|---|
| 0001863 | 5/1979 | European Pat. Off. | 568/724 V |
| 1958332 | 11/1971 | Fed. Rep. of Germany | 568/727 |
| 2048661 | 4/1972 | Fed. Rep. of Germany | 568/724 |
| 58-135832 | 8/1983 | Japan | 568/727 |
| 1081257 | 8/1967 | United Kingdom | 568/724 |
| 1377227 | 12/1974 | United Kingdom | 568/724 |

OTHER PUBLICATIONS

Patent Abstracts of Japan, vol. 7, no. 248 (C-193)(1393), Nov. 4th, 1983; JP-A-58-135832 (MITSUI TOATSU) 12-08-83.

*Primary Examiner*—Werren B. Lone
*Attorney, Agent, or Firm*—Burns, Doane, Swecker & Mathis

[57] ABSTRACT

A process for producing high-purity bisphenol A comprises reacting phenol with acetone in the presence of hydrochloric acid as the catalyst to obtain a product mixture, removing the hydrochloric acid from the product mixture, thereby yielding a liquid mixture, adding water to the liquid mixture, evaporating a water-phenol mixture from the liquid mixture under reduced pressure, thereby cooling the liquid mixture and crystallizing out the adduct of bisphenol A with phenol, and finally recovering bisphenol A from the adduct, wherein an improvement comprises treating the water-phenol mixture with a weakly basic ion-exchange resin and recycling and reusing the treated mixture as the water to be added to the liquid mixture. This process does not causes any troubles such as the corrosion of equipment and the decomposition and discoloration of bisphenol A during distillation.

4 Claims, 1 Drawing Sheet

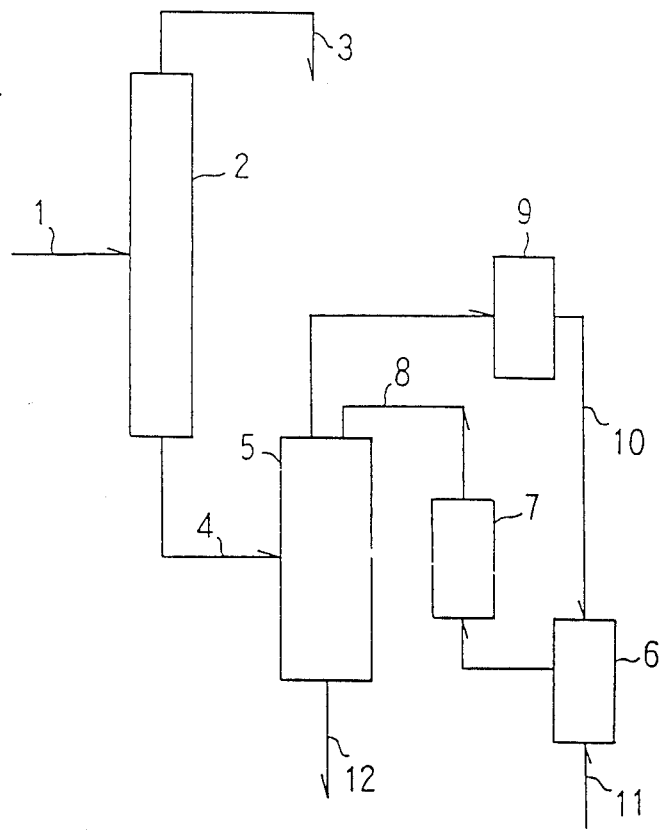

PROCESS FOR PREPARING BISPHENOL A

BACKGROUND OF THE INVENTION

The present invention relates to a process for preparing high-purity 2,2-bis(4-hydroxyphenyl)propane (referred to as bisphenol A hereinafter).

Bisphenol A is used as a raw material for polycarbonate resins and epoxy resins and also for engineering plastics Colorless and high-purity bisphenol A is required for these uses.

Bisphenol A is prepared by the reaction of acetone with excess phenol in the presence of an acid catalyst such as hydrochloric acid. The product mixture contains bisphenol A and also the catalyst, unreacted acetone, unreacted phenol, water, and other by-products such as coloring substances.

There are many known processes for obtaining high-purity bisphenol A from the product mixture. For example, in the case where hydrochloric acid has been used as the catalyst in the reaction, the product mixture is heated at 110 to 120° C. under reduced pressure, thereby removing hydrochloric acid, unreacted acetone, water, and a small amount of phenol and thereafter bisphenol A in the form of an adduct with phenol is separated by cooling. The other process includes distillation to separate bisphenol A from other substances having a higher and lower boiling point than that of bisphenol A. The thus-obtained bisphenol A may be further purified by extraction with a solvent or recrystallization from a solution.

In the case where hydrochloric acid has been used as the catalyst, the product mixture which has been distilled to remove hydrochloric acid, acetone, and water still contains a trace amount of hydrochloric acid which causes some trouble in the subsequent purification steps.

One trouble is the corrosion of equipment due to the acid. The corrosion yields metal salts which contaminate bisphenol A, and the removal of the metal salts requires a complicated purification procedure. A possible countermeasure is to use equipment made of an acid-resistant material; however, this is not economical because such equipment is expensive.

Another trouble is that bisphenol A is decomposed due to the acidic substance during distillation, as described in U.S. Pat. No. 3,073,868 and Japanese Patent Publication No. 4875/1963.

A crystallization process of the adduct of bisphenol A with phenol is disclosed in Japanese Patent Laid-open No. 135832/1983. In the process, water is added to the product mixture and the product mixture is cooled by evaporating a water-phenol mixture, thereby attaining crystallization In the evaporation step, a trace amount of hydrochloric acid distills together with water and phenol. If the distillate is discarded, hydrochloric acid does not accumulate, but discarding the distillate is economically undesirable because the phenol is lost. If the distillate is recycled and reused, hydrochloric acid accumulates and the accumulated hydrochloric acid causes some corrosion of equipment and some decomposition of bisphenol A in the subsequent steps.

SUMMARY OF THE INVENTION

It is an object of the present invention to provide a process for producing high-purity bisphenol A without causing the above-mentioned trouble (i.e., the loss of useful phenol and the accumulation of hydrochloric acid) in the step of crystallizing the adduct of bisphenol A with phenol.

To achieve the aforesaid object, we carried out a series of experiments, which led to the finding that high-purity bisphenol A can be obtained by improving the step of crystallizing the adduct of bisphenol A with phenol by evaporating a water-phenol mixture which follows the addition of water. According to the improved step, a mixture of water and phenol is recovered from the product mixture under reduced pressure, the recovered mixture is treated with a specific ion-exchange resin, and the treated mixture is recycled and reused as the water to be added to the step. The present invention was completed on the basis of this finding.

In accordance with the present invention, there is provided a process for producing high-purity bisphenol A by reacting phenol with acetone in the presence of hydrochloric acid as the catalyst to obtain a product mixture, removing the hydrochloric acid from the product mixture, thereby yielding a liquid mixture, adding water to the liquid mixture, evaporating a water-phenol mixture from the liquid mixture under reduced pressure, thereby cooling the liquid mixture and crystallizing out the adduct of bisphenol A with phenol, and finally recovering bisphenol A from the adduct, wherein an improvement comprises treating the water-phenol mixture with a weakly basic ion-exchange resin and recycling and reusing the treated mixture as the water to be added to the liquid mixture.

BRIEF DESCRIPTION OF THE DRAWINGS

The accompanying drawing is a flowsheet showing an embodiment of the process of the present invention for producing bisphenol A.

DETAILED DESCRIPTION OF THE INVENTION

According to the process of the present invention, the molar ratio of phenol to acetone in the starting mixture is from 4:1 to 12:1 usually and the reaction temperature is 40 to 70° C.

The reaction yields a product mixture containing bisphenol A, and also unreacted phenol, unreacted acetone, hydrochloric acid, water, and by-products. The product mixture is distilled under reduced pressure to remove water, acetone, hydrochloric acid, and a small amount of phenol. The vacuum distillation should be performed preferably at a pressure of 20 to 200 mmHg and a temperature of 90 to 100° C. Thus there is obtained a phenol solution of crude bisphenol A.

The thus-obtained phenol solution of crude bisphenol A is cooled to 35 to 70° C. in a crystallizer so that the adduct of bisphenol A with phenol crystallizes. The crystallization is accomplished by adding water to the crystallizer and evaporating water and phenol under reduced pressure (preferably 20 to 100 mmHg), thereby removing heat. The evaporation yields a distillate composed mainly of a mixture of water and a small amount of phenol. This mixture is treated with a weakly basic ion-exchange resin, and the treated mixture is recycled and reused as the water to be added to the crystallizer.

The amount of the water-phenol mixture to be recycled should be sufficient to cool the phenol solution of crude bisphenol A and also to remove the heat of crystallization of the adduct by its evaporation. This amount is 2 to 20 wt% of the phenol solution.

The weakly basic ion-exchange resins used in the process of the present invention should preferably be substantially insoluble in the water-phenol mixture. They include ion-exchange resins which contain secondary or tertiary amine as the exchange group, for example, "LEWATIT MP-62" (Bayer AG) and "WA-20" (Mitsubishi Chemical Industries, Ltd.). The treatment with the ion-exchange resin should preferably be carried out continuously at 20 to 70° C. The amount of the water-phenol mixture to be added to the ion-exchange resin should preferably be 0.5 to 10 kg/hr for 1 kg of the ion-exchange resin.

According to the process of the present invention, the crystals of the adduct of bisphenol A with phenol are separated by any known method, and the bisphenol A is freed of phenol.

An embodiment of the present invention will be explained with reference to the accompanying drawing.

At first, phenol and acetone are reacted in the presence of hydrochloric acid (as a catalyst). The resulting product mixture 1 is fed to a dehydrochlorination column 2 for vacuum distillation. From the top of the column 2 is removed the mixture 3 containing water, hydrochloric acid, and a small amount of phenol. From the bottom of the column 2 is obtained the mixture 4 containing bisphenol A, phenol, and by-products.

The mixture 4 enters a crystallizer 5 in which water and phenol are evaporated under reduced pressure The evaporation cools the mixture 4, crystallizing the adduct of bisphenol A with phenol. During the crystallization, the water-phenol mixture 8 is fed to the crystallizer 5 through a column 7 of a weakly basic ion-exchange resin from a phenol-water receiver 6, for the replenishment of water and phenol which evaporates in the crystallizer 5.

The water and phenol which have evaporated in the crystallizer 5 enter a condenser 9. The condensate 10 returns to the phenol-water receiver 6. In this manner, the water and phenol are recycled.

The adduct in the form of slurry 12 yielded in the crystallizer 5 is transferred to the subsequent steps. As much water as lost along with the slurry 12 is replenished by the feedwater 11 to the phenol-water receiver 6.

EXAMPLES

The invention will be described in more detail with reference to the following examples, in which "%" means "wt%", unless otherwise indicated.

EXAMPLE 1

Condensation of phenol and acetone was carried out in the presence of hydrochloric acid as the catalyst. There was obtained a product mixture composed of 54% of phenol, 35% of bisphenol A, 2% of by-products, 4% of water, and 5% of hydrochloric acid. The product mixture was fed to a dehydrochlorination column in which water, hydrochloric acid, and a small amount of phenol were removed at a pressure of 70 mmHg and a temperature of 120° C. (at the column bottom). The bottom liquid contained 10 ppm of hydrochloric acid.

The bottom liquid was continuously fed at a flow rate of 400 kg/hr to a crystallizer kept at a pressure of 50 mmHg and a temperature of 45° C. Simultaneously, the water-phenol mixture was fed at a flow rate of 40 kg/hr to the crystallizer through a column filled with 20 kg of "LEWATIT MP-62" (made by Bayer AG). The water-phenol mixture was kept at 40° C.

The water-phenol mixture which had evaporated was condensed by a condenser for recycling.

The slurry of the adduct of bisphenol A with phenol which was discharged from the crystallizer contained 2 ppm of hydrochloric acid. After washing with an equal amount of phenol, a part of the adduct was dissolved in ethanol to give a 50% solution. The solution had a Hazen color of 10 APHA.

COMPARATIVE EXAMPLE 1

The same procedure as in Example 1 was repeated to produce bisphenol A, except that the weakly basic ion-exchange resin was not used. The slurry of the adduct discharged from the crystallizer contained 10 ppm of hydrochloric acid. After washing with an equal amount of phenol, a part of the adduct was dissolved in ethanol to give a 50% solution. The solution had a Hazen color of 20 APHA.

According to the process of the present invention, the product mixture is freed of hydrochloric acid effectively. It is possible to prevent bisphenol A from being contaminated by any corrosion of equipment. Thus it is possible to produce colorless and high-purity bisphenol A.

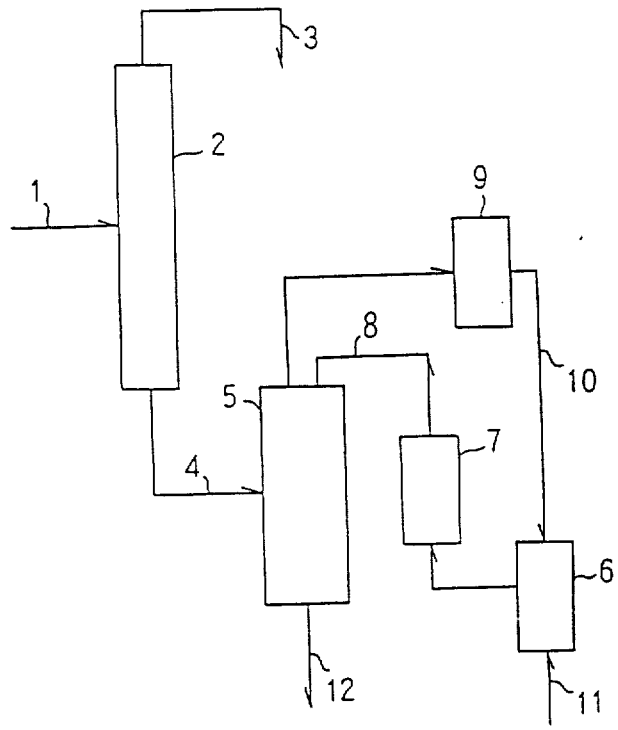

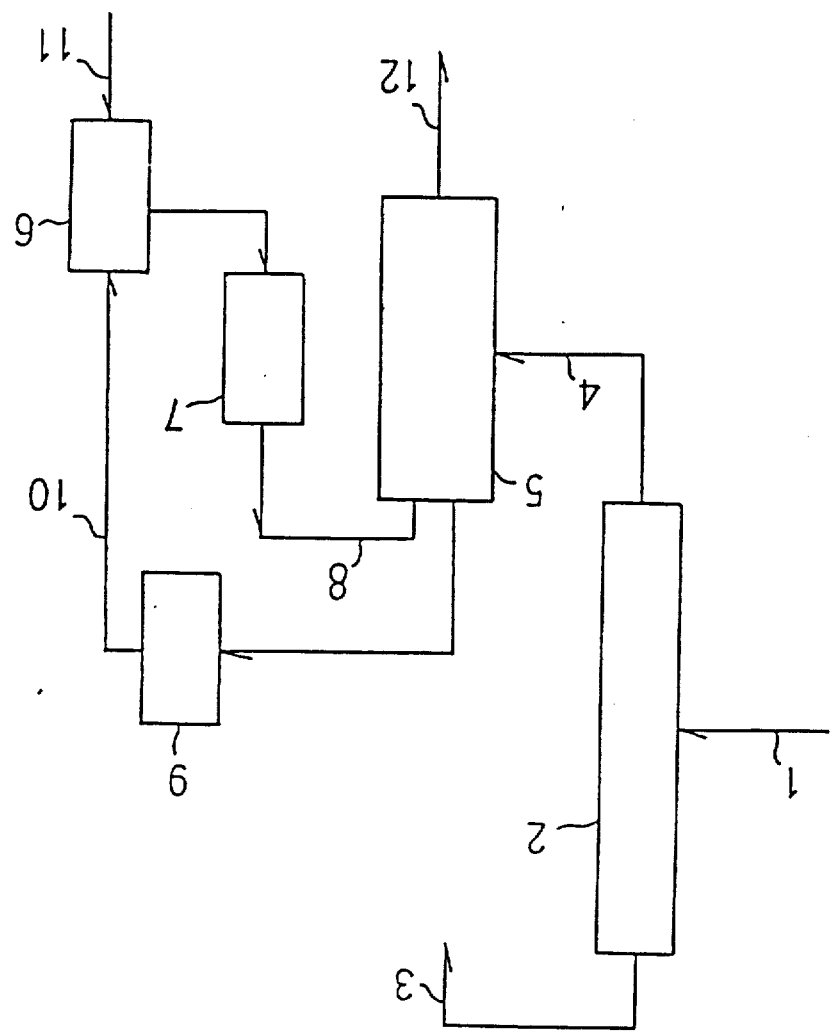

What is claimed is:

1. A process for producing high-purity bisphenol A by reacting phenol with acetone in the presence of hydrochloric acid as the catalyst to obtain a product mixture removing the hydrochloric acid from the product mixture, thereby yielding a liquid mixture, adding water to the liquid mixture, evaporating a water-phenol mixture from the liquid mixture under reduced pressure, thereby cooling the liquid mixture and crystallizing an adduct of bisphenol A with phenol, and finally recovering bisphenol A from the adduct, wherein an improvement comprises treating the water-phenol mixture with a weakly basic ion-exchange resin and recycling and reusing the treated mixture as the water to be added to the liquid mixture.

2. A process as claimed in claim 1, wherein the molar ratio of phenol to acetone in the starting mixture is from 4:1 to 12:1 and the reaction temperature is 40 to 100° C.

3. A process as claimed in claim 1, wherein the crystallization of the adduct of bisphenol A with phenol is accomplished by evaporating the water-phenol mixture at a pressure of 20 to 100 mmHg, thereby cooling the liquid mixture to 35 to 70° C.

4. A process as claimed in claim 1, wherein the amount of the water-phenol mixture recycled as the water to be added to the liquid mixture is 2 to 20 wt% of the liquid mixture.

* * * * *

UNITED STATES PATENT AND TRADEMARK OFFICE
CERTIFICATE OF CORRECTION

PATENT NO. : 4,950,804

DATED : August 21, 1990

INVENTOR(S) : Shigeru IIMURO et al

Page 1 of 3

It is certified that error appears in the above-identified patent and that said Letters Patent is hereby corrected as shown below:

The title page should be deleted to appear as per attached title page.

The sheet of Drawing consisting of Figure 1 should be added as shown on the attached sheet.

Signed and Sealed this

Twenty-ninth Day of December, 1992

*Attest:*

DOUGLAS B. COMER

*Attesting Officer*    *Acting Commissioner of Patents and Trademarks*

United States Patent

Iimuro et al.

[11] Patent Number: 4,950,804
[45] Date of Patent: Aug. 21, 1990

[54] PROCESS FOR PREPARING BISPHENOL A

[75] Inventors: Shigeru Iimuro; Yoshio Morimoto; Takashi Kitamura, all of Aichi, Japan

[73] Assignee: Mitsui Toatsu Chemicals, Inc., Tokyo, Japan

[21] Appl. No.: 310,350

[22] Filed: Feb. 14, 1989

[30] Foreign Application Priority Data

Feb. 19, 1988 [JP] Japan .................................. 63-35120

[51] Int. Cl.$^5$ ...................... C07C 37/20; C07C 37/70; C07C 39/16
[52] U.S. Cl. .................................................. 568/727
[58] Field of Search ................ 568/724, 722, 727, 728, 568/723, 749, 751

[56] References Cited

U.S. PATENT DOCUMENTS

| | | | |
|---|---|---|---|
| 3,073,868 | 1/1963 | Prahl et al. | 568/727 |
| 3,221,061 | 11/1965 | Grover et al. | 568/728 |
| 4,191,843 | 3/1980 | Kwantes | 568/728 |
| 4,364,099 | 12/1982 | Faler | 568/726 |
| 4,443,653 | 4/1984 | McLaughlin | 568/727 |

FOREIGN PATENT DOCUMENTS

| | | | |
|---|---|---|---|
| 0001863 | 5/1979 | European Pat. Off. | 568/724 V |
| 1958332 | 11/1971 | Fed. Rep. of Germany | 568/727 |
| 2048661 | 4/1972 | Fed. Rep. of Germany | 568/724 |
| 58-135832 | 8/1983 | Japan | 568/727 |
| 1081257 | 8/1967 | United Kingdom | 568/724 |
| 1377227 | 12/1974 | United Kingdom | 568/724 |

OTHER PUBLICATIONS

Patent Abstracts of Japan, vol. 7, no. 248 (C-193)(1393), Nov. 4th, 1983; JP-A-58-135832 (MITSUI TOATSU) 12-08-83.

*Primary Examiner*—Werren B. Lone
*Attorney, Agent, or Firm*—Burns, Doane, Swecker & Mathis

[57] ABSTRACT

A process for producing high-purity bisphenol A comprises reacting phenol with acetone in the presence of hydrochloric acid as the catalyst to obtain a product mixture, removing the hydrochloric acid from the product mixture, thereby yielding a liquid mixture, adding water to the liquid mixture, evaporating a water-phenol mixture from the liquid mixture under reduced pressure, thereby cooling the liquid mixture and crystallizing out the adduct of bisphenol A with phenol, and finally recovering bisphenol A from the adduct, wherein an improvement comprises treating the water-phenol mixture with a weakly basic ion-exchange resin and recycling and reusing the treated mixture as the water to be added to the liquid mixture. This process does not causes any troubles such as the corrosion of equipment and the decomposition and discoloration of bisphenol A during distillation.

4 Claims, 1 Drawing Sheet